US012569632B2

(12) United States Patent
Scheerer et al.

(10) Patent No.: US 12,569,632 B2
(45) Date of Patent: Mar. 10, 2026

(54) RESPIRATOR FOR APAP RESPIRATION USING OSCILLATORY PRESSURE

(71) Applicant: Loewenstein Medical Technology S.A., Luxembourg (LU)

(72) Inventors: Mario Scheerer, Karlsruhe (DE); Juergen Sartor, Karlsruhe (DE); Florian Landskron, Karlsruhe (DE); Matthias Schwaibold, Karlsruhe (DE)

(73) Assignee: LOEWENSTEIN MEDICAL TECHNOLOGY S.A., Luxembourg (LU)

( * ) Notice: Subject to any disclaimer, the term of this patent is extended or adjusted under 35 U.S.C. 154(b) by 2473 days.

(21) Appl. No.: 15/622,194

(22) Filed: Jun. 14, 2017

(65) Prior Publication Data

US 2017/0361041 A1     Dec. 21, 2017

(30) Foreign Application Priority Data

Jun. 16, 2016     (DE) .......................... 102016007303.9

(51) Int. Cl.
*A61M 16/06* (2006.01)
*A61M 16/00* (2006.01)
(Continued)

(52) U.S. Cl.
CPC .... *A61M 16/0006* (2014.02); *A61M 16/0051* (2013.01); *A61M 16/0066* (2013.01);
(Continued)

(58) Field of Classification Search
CPC ............ A61M 16/0006; A61M 16/161; A61M 16/0051; A61M 16/0066;
(Continued)

(56) References Cited

U.S. PATENT DOCUMENTS 5,503,146 A * 4/1996 Froehlich ............ A61M 16/024
128/202.22
5,617,846 A * 4/1997 Graetz .............. A61M 16/0069
128/204.26
(Continued)

FOREIGN PATENT DOCUMENTS

DE     202004000848 U1     4/2004
EP     0651971 A1     5/1995
(Continued)

OTHER PUBLICATIONS

Oxford Learners Dictionaries, Definition "continuously", https://www.oxfordlearnersdictionaries.com/us/definition/english/continuously, accessed Mar. 31, 2023 (Year: 2023).*

*Primary Examiner* — Elliot S Ruddie
(74) *Attorney, Agent, or Firm* — Abel Schillinger, LLP

(57) ABSTRACT

Disclosed is an autoCPAP respirator which comprises a control unit, a respiration blower and a pressure sensor. The control unit comprises a controller for generating a first control signal, which induces the speed of the blower to generate a pressurized breathing gas flow, a controller for generating a periodically variable control signal, which activates the blower such that the speed of the blower varies in an oscillating manner at a frequency in the range of 1-20 Hz, and a sensor device, which ascertains one or more of instantaneous speed, instantaneous electrical current and instantaneous electrical power of the blower to determine the breathing gas flow and/or breathing gas volume generated by the blower while using characteristic data of the blower stored in a memory.

20 Claims, 5 Drawing Sheets

(51) Int. Cl.
    *A61M 16/10*       (2006.01)
    *A61M 16/16*       (2006.01)

(52) U.S. Cl.
    CPC ...... *A61M 16/0069* (2014.02); *A61M 16/024* (2017.08); *A61M 16/161* (2014.02); *A61M 2016/0027* (2013.01); *A61M 2016/0033* (2013.01); *A61M 16/1055* (2013.01); *A61M 2205/3317* (2013.01); *A61M 2205/3334* (2013.01); *A61M 2205/3344* (2013.01); *A61M 2205/3358* (2013.01); *A61M 2205/3365* (2013.01); *A61M 2205/3368* (2013.01); *A61M 2205/3372* (2013.01); *A61M 2205/52* (2013.01); *A61M 2205/6018* (2013.01); *A61M 2205/702* (2013.01); *A61M 2230/46* (2013.01)

(58) Field of Classification Search
    CPC .. A61M 2016/0027; A61M 2016/0033; A61M 2205/3334; A61M 2205/3344; A61M 2205/3372; A61M 2205/52; A61M 16/0069; A61M 16/024; A61M 16/1055; A61M 2205/3317; A61M 2205/3358; A61M 2205/3365; A61M 2205/3368; A61M 2205/6018; A61M 2205/702; A61M 2230/46; A61M 16/0003; A61M 2016/003; A61M 2016/0036; A61M 2230/40; A61B 5/0826; A61B 5/09; A61B 2560/0247; A61B 2560/0257
    See application file for complete search history.

(56)            References Cited

U.S. PATENT DOCUMENTS

| | | | | |
|---|---|---|---|---|
| 5,694,926 A | * | 12/1997 | DeVries | A61M 16/125 128/204.21 |
| 5,704,345 A | | 1/1998 | Berthon-Jones | |
| 5,882,724 A | | 3/1999 | Graetz et al. | |
| 6,332,463 B1 | * | 12/2001 | Farrugia | A61M 16/00 128/204.18 |
| 6,401,713 B1 | * | 6/2002 | Hill | A61M 16/0069 128/204.21 |
| 6,467,477 B1 | * | 10/2002 | Frank | A61M 16/024 128/203.23 |
| 6,968,842 B1 | | 11/2005 | Truschel et al. | |
| 2004/0255943 A1 | * | 12/2004 | Morris | A61M 16/00 128/204.18 |
| 2005/0031322 A1 | * | 2/2005 | Boyle | A61M 16/0057 388/800 |
| 2007/0044799 A1 | * | 3/2007 | Hete | A61M 16/024 128/205.11 |
| 2009/0044805 A1 | * | 2/2009 | Somaiya | A61B 5/4818 128/204.22 |
| 2009/0326403 A1 | * | 12/2009 | Bassin | A61B 5/085 600/538 |
| 2010/0218767 A1 | * | 9/2010 | Jafari | A61M 16/0051 128/204.23 |
| 2010/0319697 A1 | | 12/2010 | Farrugia et al. | |
| 2012/0157794 A1 | | 6/2012 | Goodwin et al. | |
| 2014/0350429 A1 | * | 11/2014 | Truschel | A61M 16/026 600/533 |
| 2015/0107588 A1 | * | 4/2015 | Cheung | A61M 16/16 128/203.14 |
| 2015/0136136 A1 | | 5/2015 | Fleming et al. | |

FOREIGN PATENT DOCUMENTS

| | | | |
|---|---|---|---|
| EP | 0705615 | A1 | 4/1996 |
| EP | 0821977 | A1 | 2/1998 |
| EP | 1393767 | A1 | 3/2004 |
| WO | 9710019 | A1 | 3/1997 |
| WO | 2006047826 | A1 | 5/2006 |
| WO | 2008025080 | A1 | 3/2008 |
| WO | 2013042007 | A1 | 3/2013 |
| WO | 2013173219 | A1 | 11/2013 |

* cited by examiner

RESPIRATOR FOR APAP RESPIRATION USING OSCILLATORY PRESSURE

CROSS-REFERENCE TO RELATED APPLICATIONS

The present application claims priority under 35 U.S.C. § 119 of German Patent Application No. 10 2016 007 303.9, filed Jun. 16, 2016, the entire disclosure of which is expressly incorporated by reference herein.

BACKGROUND OF THE INVENTION

1. Field of the Invention

The present invention relates to a respirator for APAP respiration which uses oscillatory pressure.

2. Discussion of Background Information

EP 0 705 615 describes a method for controlling a respirator in that the oscillatory pressure amplitude, which corresponds to the breathing resistance of the patient, is continuously measured using oscilloresistometry, wherein after the determination of the individual breathing resistance value (base value of the pressure amplitude), pressurized breathing gas is supplied to the patient in the event of deviations from this value and the gas supply is ended as soon the base value is reached or approximately reached again. In this method for controlling and regulating a respirator for the treatment of sleep apnea patients, this device is only activated, i.e. breathing gas is only supplied to the patient under elevated pressure, when the breathing activity of the patient is disturbed by apnea or the breathing resistance—and therefore also the measured oscillatory pressure amplitude—changes due to occurring apnea. A disturbance of the breathing activity of the patient is accompanied by a change of the breathing resistance of the patient. This resistance is determined, without influencing the condition of the patient, reliably and reproducibly in a simple manner via the changes of the oscillatory pressure amplitude. In the course of a beginning apnea, constrictions or expansions of the airways of a patient cause changes in the phase angle of the oscillatory pressure amplitude and the respiratory flow in comparison to the corresponding base values in the event of normal or undisturbed breaths.

The respirator for the treatment of sleep apnea has a breathing mask, which is connected via a breathing hose to a pressurized gas source designed as a blower. The sensors of a device for generating, measuring, and filtering the oscillatory pressure amplitude according to the ORM principle and the phase angle are provided in the breathing hose before the breathing mask. The pressurized gas source 3 is activated by a control-regulating device, which is connected to the device and is adjustable to the individual base value of the oscillatory pressure amplitude corresponding to the breathing resistance of the patient, so that breathing gas is supplied to the patient in the event of significant changes of the phase angle. The device 5 also comprises a valveless membrane pump, using which a sinusoidal alternating flow is overlaid on the breathing flow.

EP 0 821 977, the entire disclosure of which is incorporated by reference herein, relates to a method for controlling a respirator for treatment of sleep apnea and a respirator for carrying out the method, wherein the phase angle (the time difference between respiratory flow and respiratory pressure) and the pressure amplitude corresponding to the breathing resistance are measured and also the individual breathing resistance value (base value) of the pressure amplitude of a patient is determined with the aid of oscilloresistometry and the breathing gas pressure is regulated as a function of these variables.

To carry out an ascertainment of the flow volume, using sensors having temperature-controllable heating wires, which are provided with temperature-dependent resistances, is for example known. Upon heating of one of the resistance wires, a temperature change can be detected in the region of a further heating wire, which is dependent on the respective flow volume. Detecting the flow volume via measurement bridges, which are subjected to the flow volume, having temperature-dependent resistances, is also already known, because cooling effects are also dependent on the respective flow volume here. The known sensors have proven to be relatively complex and costly, however.

It is disadvantageous that the device requires a pump, using which an oscillating alternating flow is generated. It is also disadvantageous that the signals of the oscilloresistometry have to be recorded by means of a flow and/or pressure sensor.

In view of the foregoing, it would be advantageous to have available a device with which it is possible to measure the oscillatory airway resistance during respiration therapy, without an additional generator pump or sensors for the breathing gas flow or flow.

The terms breathing gas flow and flow are used synonymously herein and in the appended claims.

SUMMARY OF THE INVENTION

The present invention provides an autoCPAP respirator which comprises a control unit, a respiration blower and a pressure sensor. The control unit comprises a controller for generating a first control signal, which induces the speed of the blower to generate a pressurized breathing gas flow, and a controller for generating a periodically variable control signal, which activates the blower such that the speed of the blower varies in an oscillating manner in the range of 1-30 Hz, preferably 1-20 Hz. Further, the control unit comprises a sensor device, which ascertains at least the current speed of the blower and/or ascertains the current electrical current of the blower and/or ascertains the current electrical power of the blower to determine the breathing gas flow and/or breathing gas volume generated by the blower by using characteristic data of the blower stored in a memory and pressure values provided by the pressure sensor.

According to the invention both a speed (number of revolutions per time unit) of the motor and pressure in the region of the flow volume are metrologically detected and supplied to the control unit, and the flow volume is ascertained by the control unit by a computed linkage of the measured values for the pressure and the speed.

It would also be advantageous to have available a device of the type mentioned at the outset such that a high measurement accuracy is achieved while using a simple sensor device.

According to the invention, the motor is provided with a sensor device for speed detection and a sensor for pressure measurement is arranged in the region of the flow volume. The sensor and the sensor device are connected to the control unit, and the control unit is provided with a computer unit for determining the flow volume and/or the flow by way of a computed linkage of the measured values for the pressure and the speed.

The metrological detection of the speed of the motor and the metrological detection of the pressure in the region of the flow volume can be performed cost-effectively and with high accuracy by structurally simple sensors. By way of the computed evaluation of these measured variables in the region of the control unit, it is possible to ascertain the respective flow volume in consideration of a mathematical model of the fluidic properties of the overall arrangement. The computation of the flow volume from the measured parameters is performed according to comparatively simple computing guidelines, so that the conversion can be carried out in a simple microprocessor, for example. Alternatively, however, it is also possible to carry out an analog ascertainment with the aid of components which have suitable characteristic curves.

An ascertainment of a present flow volume is assisted in that the computed linkage is carried out in consideration of a device characteristic, which is defined by a characteristic map.

To enable an ascertainment of the flow volume with low time expenditure, it is proposed that the characteristic map be metrologically recorded and stored in the respirator before a detection of the flow volume.

The time expenditure can be further shortened in that an actual physical dependence between the flow volume and a pressure prevailing in the region of the flow volume is approximated by a mixed quadratic equation.

To provide simple computing guidelines, it is proposed that a parameterization of the characteristic map be carried out.

The flow is not determined by means of a conventional sensor, but rather ascertained on the basis of a characteristic map from speed and pressure. For example, the pressure is ascertained at the device outlet. In the scope of this application, sensor means or sensors which ascertain the flow are therefore embodied in the form of circuits and/or computations. For example, these values, of the ascertained flow, can also be corrected on the basis of the ambient pressure. A further increase of the accuracy may be achieved if, additionally or alternatively, a correction is performed on the basis of the temperature of the breathing gas, for example at the respiration blower, and/or the ambient humidity. A further improvement may be achieved if various characteristic maps are provided depending on the accessory type: humidifier yes/no, hose type, bacterial filter yes/no, or mask type.

In addition, the ascertained flow can be modified via correction factor upon connection of a humidifier.

As set forth above, according to the present invention, the flow of breathing gas is not determined by means of a conventional sensor, but rather ascertained from speed and pressure on the basis of a characteristic map. The flow thus ascertained is checked and corrected if necessary by using at least one compensation parameter. Ambient pressure and/or temperature and/or accessory used and/or the ambient humidity and/or the leakage and/or the present treatment pressure are used as compensation parameters. For this purpose, at least one compensation parameter, preferably at least two compensation parameters, are ascertained by sensors or determined by computer or read out or input by the user.

The ascertained flow is at least temporarily adapted in consideration of the ascertained values of the compensation parameter or the compensation parameters and while using a characteristic map and/or a linear regression equation and/or multidimensional regression and/or linearization and/or quadratic/exponential equations.

Alternatively or additionally, a stored device-typical compensation parameter can be retrieved and used to adapt the ascertained flow at least temporarily.

The total flow ascertained in this manner can be further separated into mask flushing flow, undesired leakage flow, and respiratory flow.

The FOT (Forced Oscillation Technique) evaluation is performed on the basis of the respiratory flow thus ascertained. The FOT oscillation is generated using the respiration blower. The 1-30 Hz, preferably 1-20 Hz oscillation is modulated for this purpose to the treatment target pressure and is also regulated by the pressure regulator. The oscillation can also be in the range 2-10 Hz.

The target pressure is changed in an oscillating manner by the controller to generate the FOT oscillation. The pressure regulator follows with the actual pressure. At the high frequency, however, this is also subject to error. Depending on the resistance and compliance of lungs, hose, mask, airways, or other factors, the actual pressure thus oscillates at an individual amplitude which deviates somewhat. The calculated flow comes into play for the first time here. The pressure regulator estimates the pressure drop via the hose and other accessories on the basis of the calculated flow and attempts to compensate for it. It is only then possible for the pressure regulator to implement the specification of the controller thereby.

To generate the FOT oscillation, alternatively also only the speed can oscillate at a fixed amplitude.

The consistency of the airways is ascertained on the basis of the quotient of the amplitude from calculated flow and pressure. It is thus ascertained how much flow can be generated per pressure. If the airways are open, there is a large amount of flow. If they are closed, there is little flow. The threshold is at 12.5 l/min/hPa, if no leakage is present. The higher the level of leakage, the more the threshold value shifts, because more flow per pressure variation can be generated in any case in a leaky system. In this case, both are relevant: intentional leakage (flushing flow) and unintentional leakage (mouth or mask leaky).

During the apnea classification using FOT, the predefined target pressure value $P_{set}$ is overlaid with a sinusoidal oscillation at a frequency of 2-10 Hz, for example about 4 Hz.

This value (third coordinate system) is used as a target variable for the pressure regulator. With open airways, the blower has to move more air to reach the predefined pressure amplitude than in the obstructive case. Therefore, an oscillation is generated on the flow signal having greater amplitude (cf. uppermost coordinate system in FIGS. 1 and 2: in the obstructive case, the resulting flow oscillation has an amplitude of approximately 2.5 l/min, and in the case of the open airways approximately 9 l/min).

To generate a signal for the output in the obstruction channel and the classification of the apnea, the maximum value of the last 100 measurement points (this corresponds to one second) is determined both of the pressure oscillation and also the flow oscillation, and then the quotient is calculated therefrom:

$$FOTQuotient = \frac{FlowOscillation_{max}}{PressureOscillation_{max}}.$$

Alternatively or additionally, the amplitude of the last second can also be evaluated in a rolling manner for each sampling step. Alternatively or additionally, the small delta in relation to the sampling value before it can also be evaluated for each sampling value.

Alternatively or additionally, a summation over 2, 3, . . . sampling steps or an offset of multiple sampling steps via a low-pass filter for smoothing can be performed.

Alternatively or additionally, the quotient can also be computed for each sampling step or averaged over very few sampling steps. In the measurement on which the two figures are based, the quotient is approximately 5 in the obstructive case, and it is approximately 18 in the case of open airways.

This quotient is subsequently mapped on a value range from 0-100 (0 corresponds to open airways, 100 corresponds to completely blocked airways). In this case, effects which arise due to connected accessories, leaks, or environmental conditions (temperature, ambient pressure) are compensated for.

The quotient is computed per sampling step, i.e., approximately 100 times per second: change of flow versus change of pressure. At the end, it is checked whether the quotient exceeds or falls below the threshold value more than 50% of the time during the apnea.

Instead of the quotient of flow and pressure, speed and pressure, speed and flow, etc. could also be used.

The threshold value of the FOT could also be adapted depending on the type of accessory, in addition to the leakage: humidifier yes/no, bacteria filter yes/no, hose type, . . . .

In addition, there is generally an upper limit, up to which obstructive apneas are recognized. It can be fixed (e.g., 14 hPa) or variable depending on pressure limits, as a separate adjustment parameter, depending on the accessories, or depending on the event profile of the patient. For example, if the patient progressively displays obstructive apneas with increasing pressures, they are also still evaluated as obstructive apneas. However, if obstructive apnea no longer occurs via a pressure increase of a few hPa, and one suddenly occurs at still higher pressures, these are evaluated as reflexive closures due to the pressure.

DETAILED DESCRIPTION OF EXEMPLARY EMBODIMENTS

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show details of the present invention in more detail than is necessary for the fundamental understanding of the present invention, the description in combination with the drawings making apparent to those of skill in the art how the several forms of the present invention may be embodied in practice.

Figure 1:
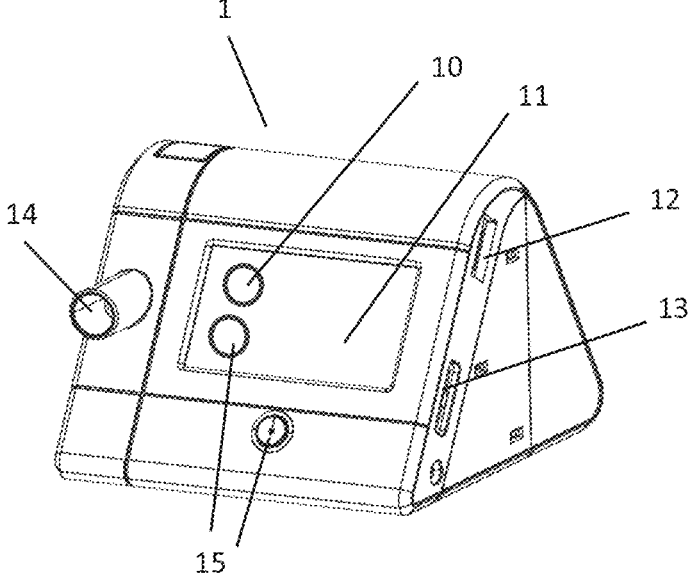
FIG. 1 shows a basic structure of a respiration device according to the invention.

FIG. 1 shows the basic structure of a device for respiration (1). A breathing gas pump is arranged in a device interior in the region of a device housing having an operating panel (10) and display (11). A connecting hose is connected via a coupling (14). An additional pressure measuring hose can extend along the connecting hose, which is connectable via a pressure inlet nozzle to the device housing. The device housing has at least one interface (12, 13) to enable a data transmission.

An operating element (15) is arranged in the region of the device housing, to be able to manually predefine a dynamic mode of the respirator. The operating element (15) can be arranged in the region of the operating panel or can be embodied as an external or separate operating element.

To avoid drying out of the airways, it has proven to be advantageous in particular during longer respiration phases to carry out humidification of the breathing air. Such humidification of the breathing air can also be implemented in other applications. A breathing air humidifier is laterally adapted for the humidification.

It is possible that the control device is suitable and designed for the purpose of monitoring a flow signal and/or a pressure signal and evaluating them on the basis of at least one algorithm, to classify an event. The flow signal and/or the pressure signal are provided in this case by at least one sensor element associated with the control device. The sensor element is provided in this case for detecting at least one flow property and/or at least one pressure property of the air flow for the respiration. The evaluation of flow signals and/or pressure signals enables a reliable recognition and classification of events of the respiration.

The control device is particularly preferably also suitable and designed to register at least one respiration parameter on the basis of the flow signal and/or the pressure signal, for example, the breathing frequency, the breath volume, the respiratory minute volume, the inspiration flow and/or the inspiration pressure and/or the airway resistance.

The control device can additionally be suitable and designed for the purpose of applying an oscillating control signal to the flow generator. The flow generator thereupon generates a breathing gas flow having a modulated pressure oscillation, which is preferably in the range of 1-20 Hz, particularly preferably 2-10 Hz, or also about 4 Hz, and causes a pressure stroke of 0.1-1 cm $H_2O$, preferably about 0.4 cm $H_2O$. This pressure stroke also induces an oscillating flow.

The control device can be suitable and designed to output a corresponding notification to a user in the event of registered breathing events. For example, the notification can be visually and/or acoustically indicated by means of a display device. The notification can also be output, for example, by means of an interface to at least one external data processing device. Such a notification is particularly advantageous, because the respiration treatment can be adapted accordingly in awareness of the events. On the other hand, if the notification does not occur, a corresponding success of the respiration treatment can be established.

The respirator can be adapted dynamically and in particular depending on the breathing phase of the user. For example, a breathing phase change can be recognized on the basis of the control device, so that a higher or lower pressure can be provided depending on the breathing phase. For example, the respirator can be designed as a CPAP or APAP device. The respirator 1 can also be designed as a bilevel device. For example, the respirator 1 reacts to determined breathing events, for example, snoring, breath flattening, and/or obstructive pressure peaks, with corresponding settings of the respiration parameters.

Using the respirator 1 shown here, events which occur in the breathing or during the respiration are recognized and classified. For this purpose, the sensor means detects one or more respiration parameters such as pressure and/or flow and/or ODS signal and supplies corresponding signals to the control device 7. The control device 7 analyzes the signals by means of suitable algorithms, so that characteristic signal curves can be recognized and classified as an event. In this case, for example, a parameter extraction can be used with reference to levels and amplitude values, time intervals, envelope curves, zero crossings, and slopes. In the case of an analysis with regard to time features, for example, periodicities and frequencies are used during a parameter extraction. An obstructive apnea (OA) is recognized if a greatly reduced flow volume is recognized and/or an ODS increase occurs for at least two breaths.

An obstructive hypopnea (OH) is shown, for example, by way of a reduced flow volume for two successive inspirations or by obstructive flattening (a typical flattening of the breathing curve) of the flow signal.

Obstructive snoring (OS) is recognized by cumulative snoring over at least two consecutive inspirations accompanied by obstructions or flattening.

Obstructive flattening (OF) is recognized by cumulative flattening over at least three inspirations, and at least one increase of the inspirational ODS signal.

An obstructive event (OE) is recognized by a significant cumulative inspirational increase of the ODS signal.

Snoring (S) is recognized by cumulative snoring (at least 3 cumulative inspirations) without inspirational ODS increase.

Nonspecific flattening (NF) is recognized by cumulative flattening (at least 3 inspirations).

A central apnea (CA) is recognized via a strongly reduced flow volume for 10 seconds without ODS increase or flattening.

A central hypopnea (CH) is recognized by a reduced flow volume (2 consecutive inspirations) without ODS increase.

A leak in the region of the patient interface or a mouth and mask leak is recognized in that the target pressure cannot be reached and/or the leak flow is greater than 0.6 l/sec.

The recognized events can then be stored in the storage device and used for a respiration statistic. One advantage of the event recognition is that an adaptation of the respiration can be performed on the basis of the classified events, for example, an automatic pressure increase in the event of an obstructive apnea. In addition, a diagnosis of determined respiratory disturbances can be performed to a certain extent.

A special advantage of the respirator 1 shown here is the control device 7, which further analyzes the recognized events and also registers Cheyne-Stokes breathing on the basis of a characteristic occurrence of the events. Such an event analysis is sketched by way of example in FIG. 2.

Figures 2, 3:
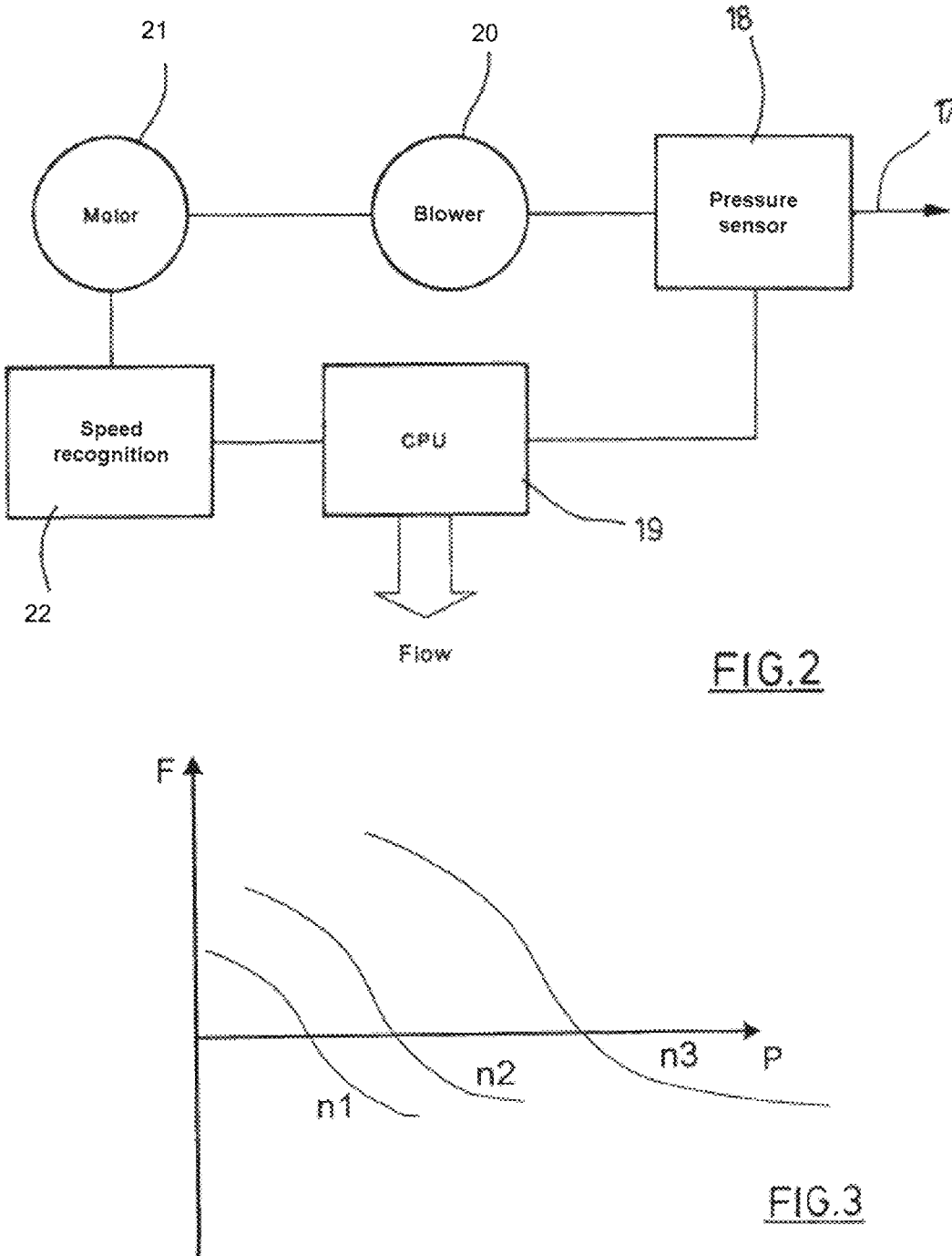
FIG. 2 is a schematic block diagram to explain a part of an internal construction of the device of FIG. 1.
FIG. 3 is a characteristic map which shows the dependence of the flow volume on the respective pressure for an exemplary respiration system.

FIG. 2 shows a schematic block diagram to explain a part of an internal construction of the device corresponding to FIG. 1. A pump device (20), which is designed as a blower, is provided for conveying the flow volume of breathing gas. The pump device (20) is driven by a motor (21). A sensor (22), which is connected to a control unit, is used to detect a speed of the motor (21). A sensor (18) for detecting a pressure is arranged in the region of a line (17), which is fed by the pump device (20), for the flow volume. The sensor (18) is also connected to the controller.

A computer unit (19) is implemented in the region of the control unit, which performs a computed linkage of the measured values for the pressure and the speed and computes a present volume flow therefrom. If the control unit is designed as a digital computer, for example a microprocessor, it is possible to implement the computer unit (19) as part of the sequence programming of the control unit. In the case of an analog design of the control unit, the intention is also to implement the computer unit (19) via components having linear or nonlinear electrical behavior.

FIG. 3 illustrates a characteristic map, which reflects the dependence of the flow volume on the respective pressure for a respiration system selected by way of example. It can be seen in particular that different characteristic curve profiles result at different speeds of the motor (21). The respective characteristic curves consist of approximately parabolic subregions, which are connected in the surroundings of the pressure axis by approximately linear curves.

Figure 4:
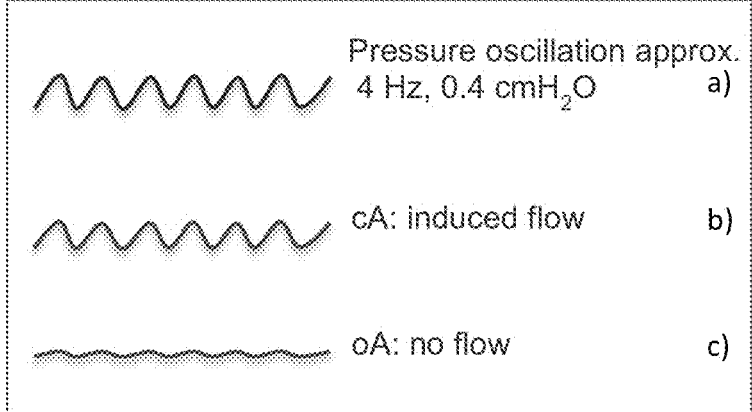
FIG. 4: shows a measured curve of the flow volume and a curve computed by a control unit of a respiratory system according to the invention.

FIG. 4 compares a measured curve of the flow volume and a curve computed by the control unit. The flow volume is indicated in this case in l/sec. It can be seen that there is a very extensive correspondence.

Figure 5A:
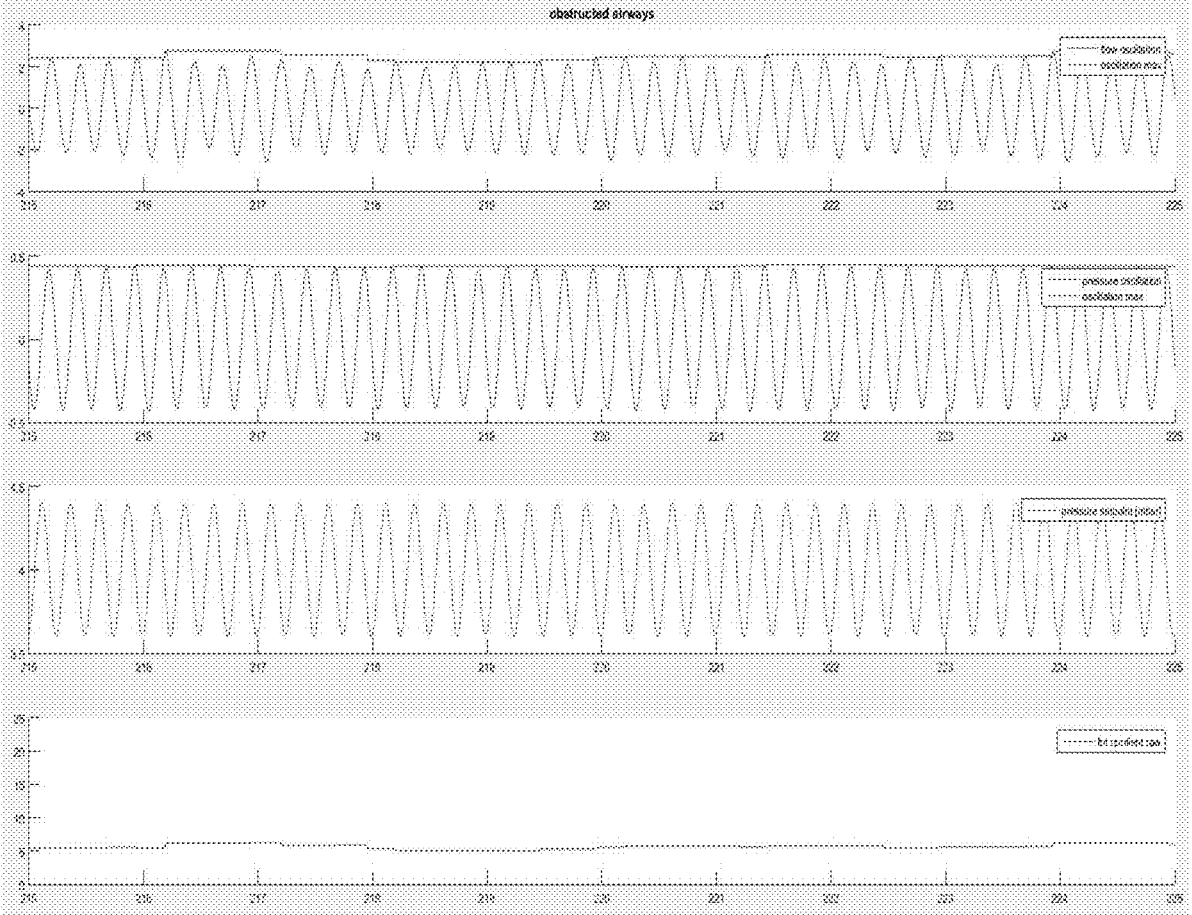
FIG. 5*a* shows an example of pressure and flow oscillation in the event of obstructed airways.
Figure 5B:
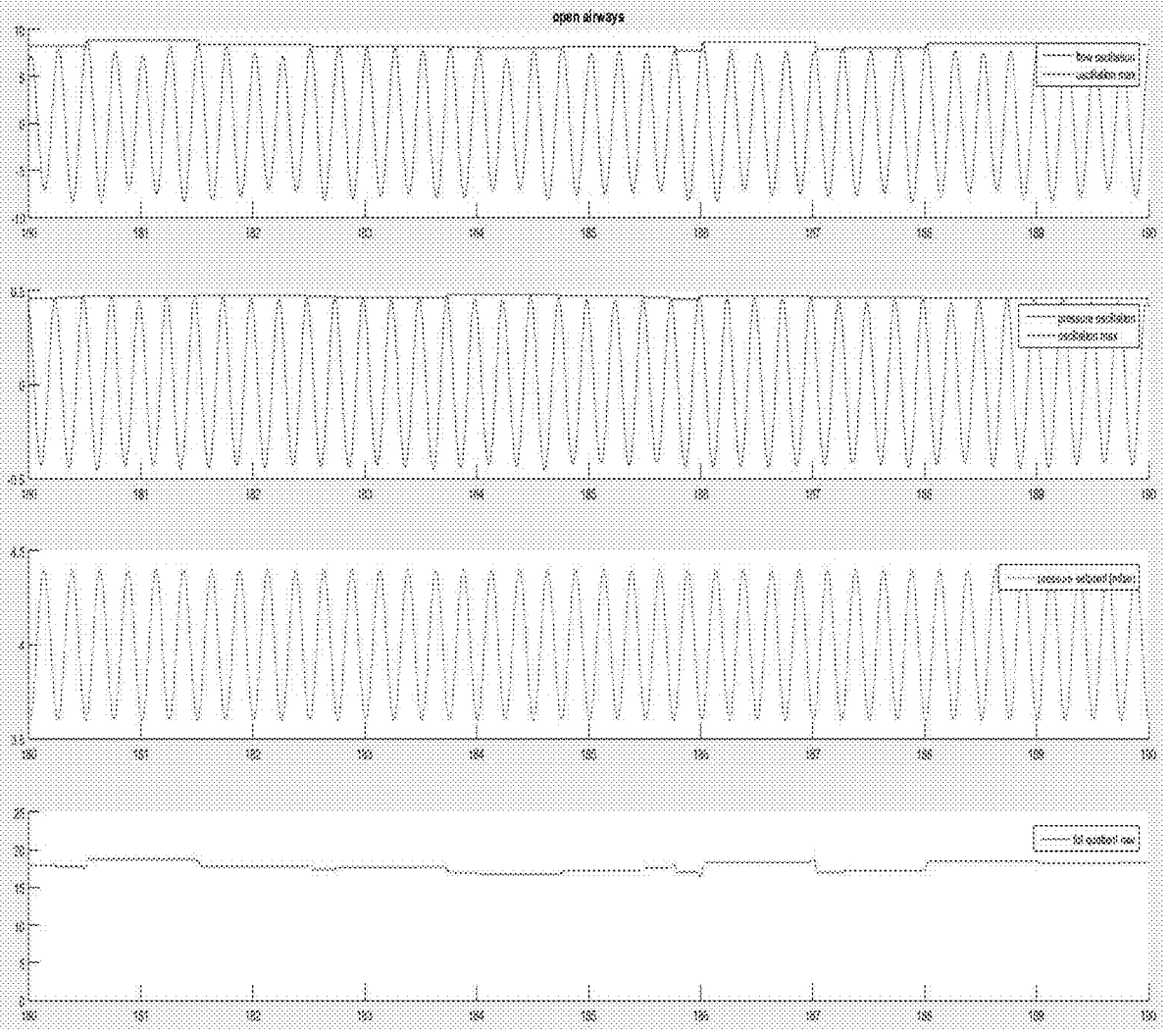
FIG. 5*b* shows an example of pressure and flow oscillation in the event of open airways.

FIG. 5a and FIG. 5b show experimentally obtained pressure and flow oscillation curves for obstructed and open airways respectively. The treatment pressure in both cases was 4 hPa (without leakage).

For an implementation of the method according to the invention and in a construction of the device according to the invention, the characteristic map is determined metrologically according to FIG. 3. For different motor speeds, the respective characteristic curve is determined in this case for the entirety of motor (21), pump device (20), line (17), and sensor (18). For the individual characteristic curves K for each speed, the pressure P results in this case as a function of the volume flow F according to the equation $$P_k(F) = a_{k2}*F^2 + a_{k1}*F + a_{k0}$$

The above equation represents an approximation of the actual curve, but it has been shown that this approximation has a good correspondence to the actual characteristic curve profile. Each of the secondary coefficients $a_{ki}$ with i=0 to 2 is dependent on the respective speed. The above equation may therefore also be represented in the form $$P(F) = a_2(n)*F^2 + a_1(n)*F + a_0(n).$$

It has been shown that the secondary coefficients $a_{ki}$ can also be determined in a good approximation from the respective speed using a quadratic equation. A corresponding equation approach reads $$a_i = b_{i2}*n^2 + b_{i1}*n + b_{i0}.$$

The primary coefficients $b_{ik}$ represent here the mechanical and electrical properties of the overall system and can be determined metrologically. In consideration of the quadratic approaches for the dependence between the pressure and the volume flow and the secondary coefficients $a_{ik}$ of the primary coefficients $b_{ik}$, a total of nine coefficients $b_{ik}$ are to be determined metrologically. The simple equation structure enables the secondary coefficients $a_{k(n)}$ to be recalculated from the known primary coefficients $b_i$ before each value for the volume flow to be recalculated. The actual value for the volume flow is then ascertained via the inverse function of the equation listed first.

What is claimed is:

1. An autoCPAP respirator, wherein the respirator comprises a control unit, a respiration blower, and a pressure sensor, the control unit comprising a first controller for generating a first control signal, which induces a speed of the blower to generate a pressurized breathing gas flow, a second controller for continuously generating a periodically variable control signal, which activates the blower such that the speed of the blower varies in an oscillating manner at a frequency in a range of 1-20 Hz, and a sensor device, which ascertains at least one of an instantaneous speed of the blower, an instantaneous electrical current of the blower, and an instantaneous electrical power of the blower, and wherein characteristic data of the blower stored in a memory, pressure values provided by the pressure sensor, and at least one of the instantaneous speed of the blower, the instantaneous electrical current of the blower, and the instantaneous electrical power of the blower are used to determine a breathing gas flow and/or breathing gas volume generated by the blower.

2. The autoCPAP respirator of claim 1, wherein both a speed of a motor and also a pressure in a region of a flow of breathing gas are metrologically detected and supplied to the control unit, the breathing gas flow and/or breathing gas volume being ascertained by the control unit by a computed linkage of measured values for the pressure and the speed.

3. The autoCPAP respirator of claim 1, wherein a motor which is provided with the sensor device for speed detection and the pressure sensor is arranged in a region of a flow, the pressure sensor and the sensor device for speed detection being connected to the control unit, and the control unit is provided with a computer unit for determining the breathing gas volume and/or the breathing gas flow by way of a computed linkage of measured values for the pressure and the speed.

4. The autoCPAP respirator of claim 1, wherein a characteristic map is metrologically recorded and stored in the respirator before a detection of a flow volume.

5. The autoCPAP respirator of claim 1, wherein the pressure is ascertained at a device outlet.

6. The autoCPAP respirator of claim 1, wherein an ascertained breathing gas flow is adapted at least temporarily in consideration of ascertained or stored values of one or more compensation parameters.

7. The autoCPAP respirator of claim 6, wherein the one or more compensation parameters comprise one or more of ambient pressure, temperature, accessories used, ambient humidity, leakage, and present treatment pressure.

8. The autoCPAP respirator of claim 6, wherein at least two compensation parameters are ascertained by sensors or determined by computer or read out or input by a user.

9. The autoCPAP respirator of claim 6, wherein the ascertained breathing gas flow is at least temporarily adapted in consideration of ascertained values of the one or more compensation parameters and while using at least one of a characteristic map, a linear regression equation, multidimensional regression, linearization, or quadratic/exponential equations.

10. The autoCPAP respirator of claim 6, wherein a stored device-typical compensation parameter is retrieved and used to adapt the ascertained breathing gas flow at least temporarily.

11. The autoCPAP respirator of claim 1, wherein values provided by the sensor device are corrected based on ambient pressure.

12. The autoCPAP respirator of claim 1, wherein values provided by the sensor device are corrected based on a temperature of a breathing gas at the respiration blower and/or ambient humidity.

13. The autoCPAP respirator of claim 1, wherein values provided by the sensor device are corrected by specific characteristic maps depending on accessory type.

14. The autoCPAP respirator of claim 1, wherein a FOT (Forced Oscillation Technique) oscillation is generated using the respiration blower and a 1-20 Hz oscillation is modulated for the purpose to achieve a treatment target pressure and is also regulated by a pressure regulator.

15. The autoCPAP respirator of claim 14, wherein the respirator is configured to estimate a pressure drop via a hose and other accessories on the basis of a calculated breathing gas flow and is configured to compensate for the pressure drop.

16. The autoCPAP respirator of claim 1, wherein a target pressure is changed in an oscillating manner by the controller to generate an FOT oscillation.

17. The autoCPAP respirator of claim 1, wherein a consistency of airways is ascertained on the basis of a quotient of an amplitude of computed breathing gas flow and pressure.

18. The autoCPAP respirator of claim 1, wherein during apnea classification with FOT, a predefined target pressure value $P_{set}$ is overlaid with a sinusoidal oscillation at a frequency of 2-10 Hz.

19. An autoCPAP respirator, wherein the respirator comprises a control unit, a respiration blower, and a pressure sensor, the control unit comprising a first controller for generating a first control signal, which induces a speed of the blower to generate a pressurized breathing gas flow, a second controller for continuously generating a periodically variable control signal, which activates the blower such that the speed of the blower varies in an oscillating manner at a frequency in a range of 1-30 Hz, and a sensor device, which ascertains at least one of instantaneous speed of the blower, instantaneous electrical current of the blower, and instantaneous electrical power of the blower, and wherein characteristic data of the blower stored in a memory, pressure values provided by the pressure sensor, and at least one of the instantaneous speed of the blower, the instantaneous electrical current of the blower, and the instantaneous electrical power of the blower are used to determine a breathing gas flow and/or breathing gas volume generated by the blower and the breathing gas flow thus ascertained is adapted at least temporarily in consideration of ascertained values of one or more compensation parameters.

20. An autoCPAP respirator, wherein the respirator comprises a control unit, a respiration blower and a pressure sensor, the control unit comprising a first controller for generating a first control signal, which induces a speed of the blower to generate a pressurized breathing gas flow, a second controller for continuously generating a periodically variable control signal, which activates the blower such that the speed of the blower varies in an oscillating manner at a frequency in a range of 1-30 Hz, and a sensor device, which ascertains at least an instantaneous speed of the blower, and wherein characteristic data of the blower stored in a memory, pressure values provided by the pressure sensor, and at least one of the instantaneous speed of the blower, the instantaneous electrical current of the blower, and the instantaneous electrical power of the blower are used to determine a breathing gas flow and/or breathing gas volume generated by the blower and the breathing gas flow thus ascertained is adapted at least temporarily in consideration of one or more compensation parameters.

* * * * *